United States Patent [19]

Nelson et al.

[11] 4,020,094
[45] Apr. 26, 1977

[54] 2-SUBSTITUTED-5-OXO-5H-DIBENZO[a,d-]CYCLOHEPTENES, THE SALTS AND ESTERS THEREOF, HAVING PHARMACEUTICAL ACTIVITY

[75] Inventors: Peter H. Nelson; Karl G. Untch, both of Los Altos, Calif.

[73] Assignee: Syntex (U.S.A.) Inc., Palo Alto, Calif.

[22] Filed: Mar. 24, 1975

[21] Appl. No.: 561,517

Related U.S. Application Data

[63] Continuation-in-part of Ser. No. 463,211, April 22, 1974, abandoned.

[52] U.S. Cl. .................. 260/469; 260/247.2 B; 260/253; 260/268 R; 260/293.62; 260/309; 260/309.6; 260/326.33; 260/429 R; 260/429.9; 260/438.1; 260/439 R; 260/448 R; 260/471 R; 260/473 R; 260/501.1; 260/501.11; 260/501.13; 260/501.15; 260/501.17; 260/501.2; 260/515 R; 424/230; 424/310; 424/316; 424/248.55; 424/317; 424/250; 424/253; 424/267; 424/273; 424/274; 424/287; 424/289; 424/295; 424/308

[51] Int. Cl.² .................. C07C 65/20; C07C 69/95

[58] Field of Search .......... 260/469, 515 R, 471 R, 260/473 R, 501.1, 501.11, 501.2, 501.13, 501.15, 501.17, 253, 268 R, 293.62, 309

[56] References Cited

UNITED STATES PATENTS

| | | | |
|---|---|---|---|
| 3,256,335 | 6/1966 | Slates et al. | 260/469 |
| 3,468,939 | 9/1969 | Kaltenbronn | 260/515 |
| 3,600,437 | 8/1971 | Marshall | 260/520 |
| 3,624,142 | 11/1971 | Shen et al. | 260/515 |
| 3,641,134 | 2/1972 | Shen et al. | 260/520 |
| 3,780,061 | 12/1973 | Allais et al. | 260/469 |
| 3,803,234 | 4/1974 | Dostert et al. | 260/469 |
| 3,933,905 | 1/1976 | Brunet et al. | 260/469 |

*Primary Examiner*—Jane S. Myers
*Attorney, Agent, or Firm*—Alan M. Krubiner; William B. Walker

[57] ABSTRACT

2-Substituted-5-oxo-5H-dibenzo[a,d]cycloheptenes represented by the following formula:

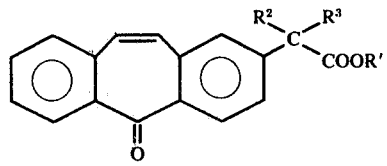

where R' is hydrogen, alkyl having 1 to 12 carbon atoms, or

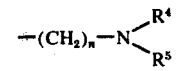

where $n$ is an integer from 2 to 4, inclusive, and $R^4$ and $R^5$ are independently lower alkyl having 1 to 6 carbon atoms or together $R^4$ and $R^5$ and the nitrogen atom to which they are attached form a heterocyclic ring having 5 or 6 total ring atoms; one of $R^2$ and $R^3$ is hydrogen and the other is hydrogen, methyl, or ethyl, or together $R^2$ and $R^3$ are methylene; and the pharmaceutically acceptable salts thereof. The compounds have anti-inflammatory, analgesic, and antipyretic activities and, accordingly, are useful in the treatment of inflammation, pain and/or pyrexia.

26 Claims, No Drawings

2-SUBSTITUTED-5-OXO-5H-DIBENZO[a,d]CY-CLOHEPTENES, THE SALTS AND ESTERS THEREOF, HAVING PHARMACEUTICAL ACTIVITY

REFERENCE TO PARENT APPLICATION

This application is a continuation-in-part of application Ser. No. 463,211, filed Apr. 22, 1974, now abandoned.

FIELD OF THE INVENTION

This invention relates to novel chemical compounds. More particularly, this invention relates to novel pharmaceutically active 5-oxo-5H-dibenzo[a,d]cycloheptene derivatives substituted at the 2-position with an acetic acid moiety or an α-substituted acetic acid moiety, and esters and pharmaceutically acceptable salts thereof.

BACKGROUND OF THE INVENTION

5-Oxo-10,11-dihydro-5H-dibenzo[a,d]cycloheptene-3-acetic acid, the 3-α-substituted acetic acids and esters and salts thereof having anti-inflammatory activity are shown by U.S. Pat. No. 3,780,061. 5-Oxo-10,11-dihydro-5H-dibenzo[a,d]-cycloheptene-2-acetic acid, the 2-α-substituted acetic acids and esters and salts thereof having anti-inflammatory activity are shown by West German OLS 2,409,919.

SUMMARY OF THE INVENTION

The novel 5-oxo-5H-dibenzo[a,d]cycloheptene-2-substituted derivatives of the present invention can be represented by the following formula:

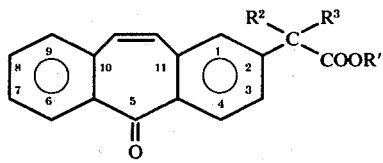

where R' is hydrogen, alkyl having 1 to 12 carbon atoms, or

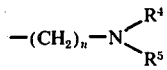

where $n$ is an integer from 2 to 4, inclusive, and $R^4$ and $R^5$ are independently lower alkyl having 1 to 6 carbon atoms or together $R^4$ and $R^5$ and the nitrogen atom to which they are attached form a heterocyclic ring having 5 or 6 total ring atoms; one of $R^2$ and $R^3$ is hydrogen and the other is hydrogen, methyl, or ethyl, or together $R^2$ and $R^3$ are methylene; and the pharmaceutically acceptable salts thereof.

As used in this specification and claims, the term "alkyl" refers to both straight and branched alkyl groups having from 1 to 6 carbon atoms (with regard to $R^4$ and $R^5$) or 1 to 12 carbon atoms (with regard to R'), and thus includes primary, secondary and tertiary alkyl groups. Typical alkyls include for example, methyl, ethyl, n-propyl, isopropyl, n-butyl, isobutyl, t-butyl, n-amyl, n-hexyl, octyl, decyl, lauryl, and the like.

The term "pharmaceutically acceptable salts" refers to salts prepared from pharmaceutically acceptable non-toxic bases including inorganic bases and organic bases. Salts derived from inorganic bases include sodium, potassium, lithium, ammonia, calcium, magnesium, ferrous, zinc, manganous, aluminum, ferric, manganic salts and the like. Copper salts are also contemplated hereby. Salts derived from pharmaceutically acceptable organic non-toxic bases include salts of primary, secondary, tertiary and quaternary amines, substituted amines including naturally occurring substituted amines, cyclic amines and basic ion exhange resins, such as triethylamine, tripropylamine, 2-dimethylaminoethanol, 2-diethylaminoethanol, ethanolamine, lysine, arginine, histidine, caffeine, procaine, N-ethylpiperidine, hydrabamine, choline, betaine, ethylenediamine, glucosamine, methylglucamine, theobromine, purines, piperazine, piperidine resins and the like. The isopropylamine salts are also contemplated hereby.

When one of $R^2$ and $R^3$ is hydrogen and the other is methyl or ethyl, the compounds of Formula I exist as pairs of enantiomorphs. Each enantiomorph or optical isomer and mixtures thereof are included within the present invention. The compounds of Formula I which exist as pairs of enantiomorphs can be administered as racemic mixtures or they can be administered as resolved enantiomorphs. In some instances, one enantiomorph exhibits greater anti-flammatory, analgesic and/or anti-pyretic activity than the other corresponding enantiomorph.

The optical isomers can be resolved by conventional means, such as selective biological degradation or by the preparation of diastereo-isomer salts or esters of the carboxylic acid with an optically active amine base, such as ($l$)-amphetamine, or an optically active alcohol, such as (d)-α-phenylethanol, and separating the diastereo-isomers by fractional crystallization. The separated diastereoisomer salts or esters are then cleaved to yield the respective optical isomers.

The compounds of Formula I exhibit anti-inflammatory, analgesic and anti-pyretic activities. Accordingly, the compositions of this invention are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compound of Formula I in an appropriate pharmaceutical composition can be via any of the accepted modes of administration of agents for the treatment of inflammation, pain or pyrexia. Thus, administration can be, for example, orally, parenterally, or topically, in the form of solid, semi-solid or liquid dosage forms, such as, for example, tablets, suppositories, pills, capsules, powders, liquid solutions, suspensions, creams, lotions, ointments, or the like, preferably in unit dosage forms suitable for simple administration of precise dosages. Tjhe compositions of this invention will include a conventional pharmaceutical carrier or excipient and an active compound of Formula I, and, in addition, may include other medicinal agents, pharmaceutical agents, carriers, adjuvants, etc.

The preferred manner of administration is oral using a convenient daily dosage regimen which can be adjusted according to the degree of affliction. Generally, a daily dose of from 0.05 mg. to 10 mg. of active compound of Formula I per kilogram of body weight is used. Most conditions respond to treatment comprising a dosage level of the order of 0.5 mg. to 5 mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

The active compound of Formula I may be formulated into a suppository using, for example, polyalkylene glycols, for example, polypropylene glycol, as the carrier. Liqiud pharmaceutically administerable compositions can, for example, be prepared by dissolving, dispersing, etc. an active compound of Formula I and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifing agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's *Pharmaceutical Sciences*, Mack Publishing Company, Easton, Pa., 14th. Edition, 1970. The composition to be administered will, in any event, contain a quantity of the active compound(s) in a pharmaceutically effective amount for relief of the particular condition being treated in accordance with the teachings of this invention.

The compounds of Formula I are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

The compounds of Formula I are also used as agents for delaying the onset of, or for postponing, parturition. As used in this application, the phrase "to delay the onset of parturition" is intended to cover that delay in parturition caused by the administration of a compound of Formula I at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time considered favorable to the mother and/or fetus.

As used in this application, the phrase "postponing parturition" is intended to cover that delay in parturition caused by the administration of a compound of Formula I after uterine muscle contractions have begun. The condition of the patient, including the time within the gestation period when the contractions have begun, the severity of the contractions and how long the contractions have taken place will affect the results achieved with the administration of a compound of Formula I. For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

With respect to animals, this treatment can also be utilized to synchronize the deliveries from a group of pregnant animals to happen at or about the same time, or to happen at or about a desired time and/or place, when the births can be handled with greater facility.

In all cases, administration of a compound of Formula I for the purposes should be consistent with best and/or accepted medical (or veterinary) practices so as to maximize the benefits to the mother and the fetus. For example, administration should not be continued so long past full term that the fetus dies in utero.

In the practice of this aspect of the present invention, a therapeutically effective amount of a compound of Formula I or a pharmaceutical composition containing a compound of Formula I is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally or parenterally in the doses and in the forms (including oral, vaginal or uterine tablets or suppositories, etc.) as set forth above regarding anti-inflammatory, etc. activities. Administration can be a single daily dose or up to three or four smaller doses regularly given throughout the day. The actual amount of active compound administered will, of course, depend on its relative activity for this particular utility.

The compounds of Formula I can be prepared by conducting an Arndt-Eistert reaction upon 5-oxo-5H-dibenzo[a,d]-cycloheptene-2-carboxylic acid to afford, in various steps thereof, 5-oxo-5H-dibenzo[a,d]cyclohepten -2-acetic acid ethyl ester and 5-oxo-5H-dibenzo[a,d]cyclohepten-2-acetic acid. 2-(5-Oxo-5H-dibenzo[a,d]cyclohepten-2-yl)propionic acid, and the corresponding esters of the aforementioned acids can be obtained via alkylation and/or esterification.

To elongate the carboxylic chain of the starting 2-carboxylic acid compound, the acid is treated with thionyl chloride to obtain the acid chloride. This acid chloride is reacted with the diazomethane to form a diazoketone which is rearranged by the action of a silver salt in the presence of an alcohol, for example, methanol or ethanol. The resultant alkyl ester of the 2-acetic acid compound can be hydrolyzed to afford the free 2-acetic acid. Or, the resultant compound can be treated with an alkali metal hydride, amide, or dialkyl amide, such as sodium hydride, lithium diisopropyl amide or sodium dimethyl amide, followed by treatment with an alkyl halide, such as methyl iodide or ethyl iodide, to α-alkylate the 2-acetic acid ester compound, thereby forming the corresponding 2-propionic acid ester or the 2-butyric acid ester, which also can be hydrolyzed to form the corresponding 2-propionic acid or 2-butyric acid compounds, respectively. The Arndt-Eistert reaction is a well-known series of steps, the particulars of which can be determined by reference to the Examples below or to the articles thereon in the published literature. The free acids can be esterified according to known procedures, for example, by treatment of the free acid or one of its functional derivatives, such as the acid chloride or the acid anhydride, with an appropriate alcohol, in the presence of an acid, dehydrating, or basic catalyst. Other methods of esterification or transesterification known to those skilled in this art can also be utilized. Alkyl esters wherein the alkyl ester moiety has 13 to 20 carbon atoms, as prepared with, for example, tridecanol, 7-tridecanol, tetradecanol, pentadecanol, 2-pentadecanol, hexadecanol, heptadecanol, 2-heptadecanol, octadecanol, nonadecanol, 2-nonadecanol and eicosanol, are also considered to be within the scope of this invention.

Also included within the novel compounds of Formula I are the corresponding dialkylaminoalkyl esters thereof which can be prepared by converting the free acid compound to the corresponding acid halide, as by treatment with thionyl chloride, and reacting the acid halide so produced with a hydroxyalkylamine, such as 2-dimethylaminoethanol or 2-diethylaminoethanol, to afford the compounds of Formula I wherein R' is

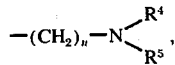

where $R^4$ and $R^5$ are independently lower alkyl. Or, the acid halide derivative can be reacted with N-(ω-hydroxyalkyl)-heterocyclic amines to afford the compounds of Formula I where $R^4$ and $R^5$ and the nitrogen atom to which they are attached form a heterocyclic ring. As used herein, the term "heterocyclic ring" refers to both unsubstituted and substituted heterocyclic rings containing at least one nitrogen ring atom and includes both saturated and unsaturated heterocyclic rings having 5 or 6 ring atoms. More specifically, the heterocyclic rings per se contemplated hereby have one nitrogen atom and four or five carbon atoms, two nitrogen atoms and three or four carbon atoms, or one nitrogen atom, one oxygen atom and four carbon atoms. Typical heterocyclic rings include, for example, 2-imidazolin-1-yl, 3-N-methyl-2-imidazolin-1-yl, pyrrolidinyl, 2-methylpyrrolidin-1-yl, morpholino, 3-methyl-morpholino, 4-N-methyl-piperazin-1-yl, 4-N-β-hydroxyethyl-piperazin-1-yl, piperidinyl, and the like.

The pharmaceutically acceptable salts are prepared by conventional techniques from pharmaceutically acceptable non-toxic bases, including metal salts such as sodium, potassium, calcium, aluminum and the like, as well as from organic amine salts, such as triethylamine, 2-dimethylaminoethanol, 2-diethylaminoethanol, lysine, arginine, histidine, caffeine, procain, N-ethylpiperidine, hydrabamine salts and the like.

The α,α-methylene group is introduced by treating the 2-acetic acid ester with an alkali metal dialkyl amide, such as lithium diisopropyl amide, in tetrahydrofuran, hexamethylphosphoramide and formaldehyde to afford the corresponding α,α-methylene acetic acid ester, which also can be hydrolzyed to form the corresponding α,α-methylene acetic acid.

The starting material (i.e., 5-oxo-5H-dibenzo[a,d]-cycloheptene-2-carboxylic acid) is prepared by esterifying 2-methylterephthalic acid with methanol, in the presence of acid catalyst, to afford the corresponding dimethyl ester which, in turn, is reacted with N-bromosuccinimide to afford 2-bromomethylterephthalic acid dimethyl ester. This diester is reacted with triphenylphosphine to afford 2,5-bis(carbomethoxy)-benzyltriphenylphosphonium bromide which is treated with benzaldehyde and diazabicyclononene to afford, after alkaline hydrolysis, cis and trans-stilbene 2,5-dicarboxylic acid. Hydrogenation of this latter compound with hydrogen over a 5% palladium on carbon catalyst affords 2-(2-phenethyl)terephthalic acid. Treatment with polyphosphoric acid yields 5-oxo-5H-dibenzo[a,d]-cycloheptane-2-carboxylic acid which can be recrystallized from aqueous dimethylformamide.

5-Oxo-5H-dibenzo[a,d]cycloheptene-2-carboxylic acid is prepared by successively treating 5-oxo-5H-dibenzo[a,d]-cycloheptane-2-carboxylic acid with diazomethane, N-bromosuccinimide, and dimethylformamide/diazabicyclononene, followed by base hydrolysis and acidification to yield 5-oxo-5H-dibenzo[a,d-]cycloheptene-2-carboxylic acid.

In each of the process steps, described herein above and below, unless otherwise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the present invention but not specifically described in this specification, will be apparent to those skilled in this art.

Exemplary of the compounds of the present invention, as represented by the structural formula above, are the following illustrative compounds:

(5-oxo-5H-dibenzo[a,d]cyclohepten-2-yl)acetic acid;

2-(5-oxo-5H-dibenzo[a,d]cyclohepten-2-yl)propionic acid;
2-(5-oxo-5H-dibenzo[a,d]cyclohepten-2-yl)butyric acid;
2-(5-oxo-5H-dibenzo[a,d]cyclohepten-2-yl)acrylic acid; methyl(5-oxo-5H-dibenzo[a,d]cyclohepten-2-yl)acetate;
ethyl(5-oxo-5H-dibenzo[a,d]cyclohepten-2-yl)acetate;
propyl(5-oxo-5H-dibenzo[a,d]cyclohepten-2-yl)acetate;
butyl(5-oxo-5H-dibenzo[a,d]cyclohepten-2-yl)acetate;
isopentyl(5-oxo-5H-dibenzo[a,d]cyclohepten-2-yl)-acetate; -acetate;
methyl 2-(5-oxo-5H-dibenzo[a,d]cyclohepten-2-yl)propionate;
ethyl 2-(5-oxo-5H-dibenzo[a,d]cyclohepten-2-yl)propionate;
propyl 2-(5-oxo-5H-dibenzo[a,dcyclohepten-2-yl)propionate;
butyl 2-(5-oxo-5H-dibenzo[a,d]cyclohepten-2-yl)propionate;
isopentyl 2-(5-oxo-5H-dibenzo[a,d]cyclohepten-2-yl)-propionate;
methyl 2-(5-oxo-5H-dibenzo[a,d]cyclohepten-2-yl)butylrate;
ethyl 2-(5-oxo-5H-dibenzo[a,d]cyclohepten-2-yl)butyrate;
propyl 2-(5-oxo-5H-dibenzo[a,d]cyclohepten-2-yl)butyrate;
butyl 2-(5oxo-5H-dibenzo[a,d]cyclohepten-2-yl)butyrate;
isopentyl 2-(5-oxo-5H-dibenzo[a,d]cyclohepten-2-yl)butyrate;
methyl 2-(5oxo-5H-dibenzo[a,d]cyclohepten-2-yl)acrylate;
ethyl 2-(5-oxo-5H-dibenzo[a,d]cyclohepten-2-yl)acrylate;
propyl 2-(5-oxo-5H-dibenzo[a,d]cyclohepten-2-yl)acrylate;
butyl 2-(5-oxo-5H-dibenzo[a,d]cyclohepten-2-yl)acrylate;
isopentyl 2-(5-oxo-5H-dibenzo[a,d]cyclohepten-2-yl)acrylate;
β-N,N-dimethylaminoethyl(5-oxo-5H-dibenzo[a,d]cyclohepten-2-yl)acetate;
β-N,N-diethylaminoethyl(5-oxo-5H-dibenzo[a,d]cyclohepten-2-yl)acetate;
β-N,N-dimethylaminoethyl 2-(5-oxo-5H-dibenzo[a,d-]cyclohepten-2-yl)propionate;
β-N,N-diethylaminoethyl 2-(5-oxo-5H-dibenzo[a,d-]cyclohepten-2-yl)propionate;
β-N,N-dimethylaminoethyl 2-(5-oxo-5H-dibenzo[a,d-]cyclohepten-2-yl)butyrate;
β-N,N-diethylaminoethyl 2-(5-oxo-5H-dibenzo[a,d-]cyclohepten-2-yl)butyrate;
β-N,N-dimethylaminoethyl 2-(5-oxo-5H-dibenzo[a,d-]cyclohepten-2-yl)acrylate;
β-N,N-diethylaminoethyl 2-(5-oxo-5H-dibenzo[a,d-]cyclohepten-2-yl)acrylate;
sodium (5-oxo-5H-dibenzo[a,d]cyclohepten-2-yl)acetate;
potassium (5-oxo-5H-dibenzo[a,d]cyclohepten-2-yl)-acetate;
calcium(5-oxo-5H-dibenzo[a,d]cyclohepten-2-yl)acetate;
sodium 2-(5-oxo-5H-dibenzo[a,d]cyclohepten-2-yl)propionate;
potassium 2-(5-oxo-5H-dibenzo[a,d]cyclohepten-2-yl)-propionate;
calcium 2-(5-oxo-5H-dibenzo[a,d]cyclohepten-2-yl)propionate;
sodium 2-(5-oxo-5H-dibenzo[a,d]cyclohepten-2-yl)butyrate;
potassium 2-(5-oxo-5H-dibenzo[a,d]cyclohepten-2-yl)-butyrate;
calcium 2-(5-oxo-5H-dibenzo[a,d]cyclohepten-2-yl)butyrate;
sodium 2-(5-oxo-5H-dibenzo[a,d]cyclohepten-2-yl)acrylate;
potassium 2-(5-oxo-5H-dibenzo[a,d]cyclohepten-2-yl)-acrylate;
calcium 2-(5-oxo-5H-dibenzo[a,d]cyclohepten-2-yl)acrylate;

and the corresponding d and l isomers of those compounds which have an assymetric carbon atom.

Of these compounds 2-(5-oxo-5H-dibenzo[a,d]cyclohepten-2-yl)propionic acid and the corresponding d isomer thereof are presently preferred because of the substantial anti-inflammatory activity thereof.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION 1

148 G. of 2-methylterephthalic acid is refluxed for 24 hrs. in 750 ml. of dry methanol containing 30 ml. of sulphuric acid. The solution is cooled, poured into water and extracted with ether. The extract is washed, dried and evaporated to give dimethyl-2-methylterephthalate.

88 G. of dimethyl-2-methylterephthalate in 1000 ml. of carbon tetrachloride containing 89 g. (1 eq.) of N-bromosuccinimide is refluxed for 3 hours using a heat lamp. The solution is cooled, filtered and evaporated to dryness to give dimethyl-2-bromomethylterephthalate.

25.7 G. of dimethyl-2-bromomethylterephthalate is refluxed in 250 ml. of acetonitrile containing 26.2 g. (1 eq.) of triphenylphosphine for 4 hrs. The solution is cooled and diluted with 1250 ml. of ether thereby precipitating 2,5-bis(carbomethoxy)-benzyltriphenylphosphonium bromide which is filtered off and dried under vacuum.

51.9 G. of 2,5-bis(carbomethoxy)-benzyltriphenylphosphonium bromide and 10.6 g. of benzaldehyde are stirred in 300 ml. of acetonitrile and 12.4 g. of diazabicyclononene is added. The mixture is heated briefly to reflux, then cooled and evaporated to an oil. The oil is dissolved in ethyl acetate, and the solution washed with dilute hydrochloric acid, dried and evaporated. The residue is refluxed for 12 hrs. in a solution of 20 g. of potassium hydroxide in 300 ml. of water and 50 ml. of methanol. The solution is cooled and extracted with chloroform. The aqueous solution is acidified with dilute hydrochloric acid and the precipitated cis and trans stilbene-2,5-dicarboxylic acid is filtered off and dried.

23.6 G. of cis and trans -stilbene-2,5-dicarboxylic acid is dissolved in 100 ml. of dimethylformamide containing 500 mg. of 5% palladium on carbon and hydrogenated for 2 hrs. The solution is filtered and evaporated to dryness to give a crude product which upon recrystallization from aqueous ethanol yields 2-(2-phenethyl)terephthalic acid.

23.8 G of 2-(2-phenethyl)terephthalic acid is dissolved in 200 ml. of sulpholane at 130° C and 150 ml. of polyphosphonic acid is added with stirring. The mixture is stirred at 130° C for 4 hrs., then poured into 1000 ml. of water. The product is filtered off and recrystallized from aqueous dimethylformamide to yield 5-oxo-5H-dibenzo[a,d]-cycloheptane-2-carboxylic acid (m.p. 203°–204° C).

PREPARATION 2

5.0 G. of 5-oxo-5H-dibenzo[a,d]cycloheptane-2-carboxylic acid (as prepared in Preparation 1 above) is suspended in 50 ml. of dioxane, added to excess ethereal diazomethane, and stirred until dissolution is complete. The solution is then evaporated to dryness to yield 2-carbomethoxy-5-oxo-5H-dibenzo[a,d]cycloheptane.

4.68 G. of 2-carbomethoxy-5-oxo-5H-dibenzo[a,d]-cycloheptane is refluxed in 100 ml. of carbon tetrachloride containing 3.56 g. (1 eq.) of N-bromosuccinimide while being irradiated with a 100 watt incandescent lamp. After 2 hrs. the solution is cooled, filtered and evaporated to dryness. The residue is dissolved in 30 ml. of dimethylformamide and 2.48 g. (1 eq.) of diazabicylononene is added. The mixture is heated briefly to 60° C, and water and ethyl acetate are added. The organic layer is washed with dilute hydrochloric acid and water, then dried and evaporated to give 2-carbomethoxy-5-oxo-5H-dibenzo[a,d]cycloheptene. Hydrolysis in eight to one aqueous methanol, 5% potassium hydroxide, followed by acidification with dilute hydrochloric acid yields 5-oxo-5H-dibenzo[a,d]cycloheptene-2-carboxylic acid (m.p. 261°–262° C).

EXAMPLE I

22 G. of 5-oxo-5H-dibenzo[a,d]cycloheptene-2-carboxylic acid is stirred in 200 ml. of chloroform, 50 ml. of thionyl chloride and 1 ml. of dimethylformamide for 8 hrs. The mixture is evaporated to dryness and the residue recrystallized from acetonitrile to yield 2-chloroformyl-5-oxo-5H-dibenzo[a,d]cycloheptene. This is dissolved in 200 ml. of chloroform and added to a 3-fold excess of ethereal diazomethane at 0° C. The mixture is left at 0° C for 12 hrs. then evaporated to dryness. The residue is recrystallized from acetonitrile to yield 2-diazoacetyl-5-oxo-5H-dibenzo[a,d]cycloheptene. The diazoketone is heated to reflux in 250 ml. of ethanol and a saturated triethylamine solution of 2 g. of silver benzoate is added slowly until gas evolution ceases. The solution is cooled, filtered and evaporated to yield ethyl (5-oxo-5H-dibenzo[a,d]cyclohepten-2yl)acetate. This ester is refluxed in 5% aqueous potassium hydroxide for 12 hrs. The solution is cooled, acidified with dilute hydrochloric acid and extracted with ether. The ether extract is dried and evaporated to yield (5-oxo-5H-dibenzo[a,d]cyclohepten-2-yl)acetic acid which can be recrystallized from acetone-hexane (m.p. 148°–149.5° C).

EXAMPLE II

Lithium isopropylcyclohexylamide is prepared by adding 10 mls. of 1.0 molar n-butyllithium to a solution of 1.41 g. of isopropylcyclohexylamine in 100 ml. of dry tetrahydrofuran. To this solution, cooled to −80° C,
there is added a solution of 2.94 g. of ethyl (5-oxo-5H-dibenzo[a,d]cyclohepten-2yl)acetate (as prepared in Example I above) in 10 ml. of tetrahydrofuran. The mixture is left for 5 minutes, then 1.42 g. of methyl iodide is added. The reaction mixture is allowed attain room temperature, then water and ether are added. The ethereal layer is washed with dilute hydrochloric acid and water, dried and evaporated to yield ethyl 2-(5-oxo-5H-dibenzo[a,d]cyclohepten-2-yl)propionate. This ethyl ester is refluxed for 12 hrs. in 5% aqueous potassium hydroxide, followed by acidification with dilute hydrochloric acid and ether extraction to afford dl 2-(5-oxo-5H-dibenzo[a,d]cyclohepten-2-yl)propionic acid (m.p. 138°–139° C, 113°–115° C). This mixture of optical isomers can exist in two crystalline forms. The form having the higher melting point is obtained by using chloroform/hexane as the recrystallizing solvent, while the form having the lower melting point is obtained by using acetone/hexane as the recrystallizing solvent.

EXAMPLE III 1.075 Ml. of 1.6 molar n-butyllithium in hexane is added to a solution of 0.242 ml. of diisopropylamine in 15 ml. of dry tetrahydrofuran. 0.300 Ml. of hexamethylphosphoric triamide is added and the mixture is cooled to about −60° C. 0.465 G. of methyl (5-oxo-5H-dibenzo[a,d]-cyclohepten-2-yl)acetate is added, and after 15 minutes, 0.137 ml. of ethyl iodide is added. The mixture is warmed slowly to room temperature and a further 0.05 ml. of ethyl iodide is added. After 30 minutes an additional 0.05 ml. of ethyl iodide is added. After 30 minutes, a few drops of methanol are added, and then ether and water are added. The organic layer is washed with water, dilute hydrochloric acid and saturated sodium chloride solution, then dried and evaporated to yield the impure product, which, after chromatography on 40 g. silica gel, eluting with hexane:ether (5:1) affords methyl 2-(5-oxo-5H-dibenzo[a,d]cyclohepten-2-yl)butyrate. 0.326 G. of methyl 2-(5-oxo-5H-dibenzo[a,d]cyclohepten-2-yl)butyrate is refluxed for 4 hours in 10 ml. of methanol and 20 ml. of water containing 0.5 g. of sodium hydroxide. The mixture is cooled, washed with ether and acidified with dilute hydrochloric acid. The product is extracted with ether and the extract washed, dried and evaporated to yield 2-(5-oxo-5H-dibenzo[a,d]cyclohepten-2-yl)butyric acid (m.p. 147°–148° C).

EXAMPLE IV 1.25 Ml. of 1.6 molar n-butyllithium in hexane is added to a solution of 0.280 ml. of diisopropylamine in 30 ml. of tetrahydrofuran. The solution is cooled to −80° C and 0.556 g. of methyl (5-oxo-5H-dibenzo[a,d-]cyclohepten-2-yl)acetate is added. After 10 minutes 0.38 ml. of hexamethylphosphoric triamide is added. The cooling bath is removed and formaldehyde vapor, entrained in nitrogen, is passed over the solution until it becomes colorless. Water and ether are then added and the organic layer is washed with dilute hydrochloric acid, saturated sodium chloride solution, then dried and evaporated. The residue is chromatographed on 10 g. of silica gel, eluting with hexane: ethyl acetate (5:1) to isolate methyl 2-(5-oxo-5H-dibenzo[a,d]cyclohepten-2-yl)acrylate (m.p. 153°–156° C). 0.02 G. of this compound is refluxed under nitrogen in 5 ml. of water, 2 ml. of ethanol and 0.5 ml. of saturated sodium carbonate solution for 4 hours. The mixture is cooled, washed with ether and acidified with dilute hydrochloric acid, then extracted with ethyl acetate and the extract dried and evaporated to yield 2-(5-oxo-5H-dibenzo[a,d]cyclohepten-2yl)acrylic acid (m.p. 232°–235° C).

EXAMPLE V 1.0 G. of (5-oxo-5H-dibenzo[a,d]cyclohepten-2yl)-propionic acid is dissolved in 25 ml. of chloroform, and 1 ml. of thionyl chloride and 0.1 ml. of dimethylformamide are added thereto. The mixture is left for 3 hrs., then evaporated to dryness. The residue is dissolved in 20 ml. of benzene and evaporated to dryness. 0.5 G of the residue is dissolved in 5 ml. of acetonitrile containing 1.0 ml. of isopentylalcohol and 1.0 ml. of triethylamine. The mixture is left at room temperature for 16 hrs., then poured into water. The solution is extracted with ether and the extract washed with water, dilute hydrochloric acid, aqueous sodium carbonate, dried and evaporated to yield the crude product which is dissolved in hexane:ether (1:1), the solution passes through silica gel, and the eluant evaporated to afford isopentyl (5-oxo-5H-dibenzo[a,d]cyclohepten-2-yl)propionate [an oil; n.m.r. spectrum in deuterochloroform relative to tetramethylsilane: 0.87 (doublet $CH[CH_3]_2$; 1.57 (doublet, $CHCH_3$) and 7.23 ppm (singlet 10H,11H); mass spectrum: 348(M+), 278, 234, 233, 205].

In similar manner substituting methanol, 2-propanol, ethanol, butanol, 2-butanol, 3-methylbutanol, pentanol, 2-pentanol, 3-pentanol, 3-ethylpentanol, hexanol, 2-hexanol, 3-hexanol, heptanol, 2-heptanol, 3-heptanol, 4-heptanol, octanol, 2-octanol, 4-octanol, nonanol, 4-nonanol, 5-nonanol, decanol, 2-decanol, 3-decanol, 4-decanol, 5-decanol, undecanol, dodecanol, phenol and methyl salicylate, the corresponding esters of (5-oxo-5H-dibenzo[a,d]cyclohepten-2-yl)propionic acid are obtained including methyl (5-oxo-5H-dibenzo[a,d]cyclohepten-2-yl)propionate (m.p. 37°–39° C) and dodecyl 2-(5-oxo-5H-dibenzo[a,d]cyclohepten-2-yl)propionate [an oil; n.m.r. spectrum in deuterochloroform relative to tetramethylsilane: 0.85 (triplet, $CH_2CH_3$); 1.18 (singlet, $(CH_2)_9$); 1.53 (doublet $CHCH_3$) and 7.03 ppm (singlet, 10H,11H); mass spectrum: 446(M+), 279, 278, 234, 233, 205].

Also in similar manner, substituting any of the acids prepared herein for the (5-oxo-5H-dibenzo[a,d]cyclohepten-2-yl)propionic acid of this Example, the corresponding esters thereof are prepared, including methyl 2-(5-oxo-5H-dibenzo[a,d]cyclohepten-2-yl)acetate (m.p. 67°–69° C).

EXAMPLE VI 2-(5-Oxo-5H-dibenzo[a,d]cyclohepten-2-yl)propionyl chloride is dissolved in 25 ml. of acetonitrile with stirring, and treated with 1.0 ml. of dimethylethanolamine and 1.0 ml. of triethylamine. After the solution is stirred for 16 hours, it is added to a water/ether mixture, and the organic phase washed with water and then dried and evaporated to give a crude product which after chromatography on 10 g. silica gel, eluting with chloroform then chloroform: methanol (9:1), affords β-N,N,-dimethylaminoethyl 2-(5-oxo-5H-dibenzo[a,d]cyclohepten-2-yl)propionate as an oil (hydrochloride salt: m.p. 136°–137° C; see Example XIV).

In similar manner substituting diethylethanolamine and N-ethyl-N-methylethanolamine for the dimethylethanolamine, there is obtained β-N-N-diethylaminoethyl-2-(5-oxo-5H-dibenzo[a,d]cyclohepten-2-yl)propionate as an oil (hydrochloride salt: m.p. 117°–123° C; see Example XIV) and β-N-ethyl-N-methylaminoethyl 2-(5-oxo-5H-dibenzo[a,d]cyclohepten-2-yl)-propionate [an oil; n.m.r. spectrum in deuterochloroform relative to tetramethylsilane: 0.94 (triplet, $CH_2CH_3$); 1.53 (doublet, $CHCH_3$); 2.08 (singlet, $N-CH_3$); 4.17 (triplet, $OCH_2$) and 7.03 ppm (singlet, 10H,11H); mass spectrum: 363 (M+), 305, 233, 205].

In similar manner substituting any of the other acids prepared herein for the 2-(5-oxo-5H-dibenzo[a,d]cyclohepten-2-yl)propionic acid there are obtained the corresponding β-N,N-dimethylaminoethyl, β-N,N-diethylaminoethyl and β-N,N-ethylmethylaminoethyl esters thereof.

Also in a similar manner substituting 4-N,N-dimethylamino-butan-1-ol for the N-methyl-N-ethyl-ethanolamine, there is obtained 4'-N,N-dimethylaminobut-1'-yl 2-(5-oxo-5H-dibenzo[a,d]cyclohepten-2-yl) propionate [an oil; n.m.r spectrum in deuterochloroform relative to tetramethylsilane: 1.52 (doublet, $CHCH_3$); 2.30 (singlet, $N[CH_3]_2$); 7.03 ppm (singlet, 10H,11H); mass spectrum: 377(M+), 278, 234, 233, 205].

EXAMPLE VII

Example VI is repeated except 1-β-hydroxyethyl-2-imidazoline; 1-β-hydroxyethyl-3-methyl-2-imidazoline; 1-β-hydroxyethyl-pyrrolidine; 1-β-hydroxyethyl-2-methyl-pyrrolidine; 4-β-hydroxyethylmorpholine; 4-β-hydroxyethyl-3-methylmorpholine; 1-β-hydroxyethyl-4-methyl-piperazine; and 1-β-hydroxyethyl-piperidine; are respectively substituted for the dimethylethanolamine of Example VI, to thereby afford:

2-(2-imidazolin-1-yl)ethyl 2-(5-oxo-5H-dibenzo[a,d]cyclohepten-2-yl)propionate;

2-(3-methyl-2-imidazolin-1-yl)ethyl 2-(5-oxo-5H-dibenzo[a,d]cyclohepten-2-yl)propionate;

2-(pyrrolidin-1-yl)ethyl 2-(5-oxo-5H-dibenzo[a,d]cyclohepten-2-yl)propionate [an oil; n.m.r. spectrum in deuterochloroform relative to tetramethylsilane: 1.55 (doublet, $CHCH_3$); 7.03 ppm (singlet, 10H,11H); mass spectrum: (377(M+), 278, 234 233, 205].

2-(2-methyl-pyrrolidin-1yl)ethyl 2-(5-oxo-5H-dibenzo[a,d]cyclohepten-2-yl)propionate;

2-(morpholino) ethyl 2-(5-oxo-5H-dibenzo[a,d]cyclohepten-2-yl)propionate;

2-(3-methyl-morpholino)ethyl 2-(5-oxo-5H-dibenzo[a,d]cyclohepten-2-yl)propionate;

2-(4-methyl-piperazin-1-yl)ethyl 2-(5-oxo-5H-dibenzo[a,d]cyclohepten-2-yl)propionate; and 2-(piperid-1-yl)ethyl 2-(5-oxo-5H-dibenzo[a,d]cyclohepten-2-yl)propionate [an oil; n.m.r. spectrum in deuterochloroform relative to tetramethylsilane: 1.43, 1.51 (doublet, $CHCH_3$); 2.40, 2.50, 2.62 (triplet, $CH_2N$); 4.10, 4.20, 4.30 (triplet, $CH_2O$) and 7.18 ppm (singlet, 10H,11H); mass spectrum 389 (M+), 305, 233, 205].

EXAMPLE VIII 0.278 G. of 2-(5-oxo-5H-dibenzo[a,d]cyclohepten-2-yl)-propionic acid is added to a solution of 0.084 g. of sodium bicarbonate in 2 ml. of water. About 20 ml. of benzene is added and the mixture evaporated to dryness. This process is repeated several times, and the residue is recrystallized from methanol/ether to afford sodium 2-(5-oxo-5H-dibenzo[a,d]cyclohepten-2-yl)propionate (m.p. 145°–148° C). By employing 0.327 g. of potassium bicarbonate in place of the sodium bicarbonate above, there is obtained potassium 2-(5-oxo-5H-dibenzo[a,d]cyclohepten-2yl)propionate.

In similar manner, substituting any of the other acids prepared herein for the 2-(5-oxo-5H-dibenzo[a,d]cyclohepten-2-yl)propionic acid, there is obtained the corresponding sodium or potassium salt thereof.

EXAMPLE IX 25.2 G. of sodium 2-(5-oxo-5H-dibenzo[a,d]cyclohepten-2-yl)propionate in 300 ml. of water is added to a mixture of 5.55 g. of calcium chloride in 300 ml. of water, and the mixture is allowed to stand for 12 hrs. at room temperature. The mixture is then filtered, and the filtered salt washed several times with portions of ice cold water. The washed salt is dried under vacuum to yield calcium 2-(5-oxo-5H-dibenzo[a,d]cyclohepten-2-yl)propionate.

In similar manner, substituting any of the sodium salts of the other acids prepared herein for the sodium 2-(5-oxo-5H-dibenzo[a,d]cyclohepten-2-yl)propionate used above, there is obtained the corresponding calcium salt thereof.

EXAMPLE X 0.45 G. of 2-(5-oxo-5H-dibenzo[a,d]cyclohepten-2-yl)propionic acid was dissolved in ethyl acetate and isopropylamine is added dropwise until no more precipitate is formed. The precipitate is filtered off and recrystallized from acetone to afford isopropylammonium 2-(5-oxo-5H-dibenzo[a,d]cyclohepten-2-yl)propionate (m.p. 176°–180° C).

In similar manner, substituting 0.24 g. of lysine, 0.29 g. arginine, 0.32 g. of caffeine, 0.1 g. of ethanolamine, 0.16 g. of 2-(diethylamino)ethanol, 0.15 g. of 2-(dimethylamino)ethanol, 0.32 g. of methyl glucamine, or 0.1 g. of ethylenediamine, in place of the isopropylamine above, the corresponding salts of 2-(5-oxo-5H-dibenzo[a,d]cyclohepten-2-yl)propionic acid are obtained.

Also in similar manner, substituting any of the other acids prepared herein for the 2-(5-oxo-5H-dibenzo[a,d]cyclohepten-2-yl)propionic acid, the corresponding salts thereof are prepared.

EXAMPLE XI

To a solution of 2 ml. of trifluoroacetic anhydride in 10 ml. of benzene is added 1 g. of 2-(5-oxo-5H-dibenzo[a,d]cyclohepten-2-yl)propionic acid followed by 1 g. of salicylic acid. After 1 hour at room temperature, the benzene solution is washed with water and evaporated to dryness. The residue is recrystallized from acetone:hexane to yield 2'-carboxyphenyl 2-(5-oxo-5H-dibenzo[a,d]cyclohepten-2-yl)propionate.

Also in similar manner, substituting methyl salicylate for the salicylic acid, the corresponding esters of the acids prepared herein, including 2'-carbomethoxyphenyl 2-(5-oxo-5H-dibenzo[a,d]cyclohepten-2-yl)propionate, are prepared.

EXAMPLE XII 2.78 G. (0.01 mole) of 2-(5-oxo-5H-dibenzo[a,d]cyclohepten-2-yl)propionic acid is dissolved in 25 ml. of isopropanol and 1.35 g. (0.01 mole) of l-amphetamine is added. The salt crystallizes out and is filtered off and recrystallized several times to constant specific rotation. The salt is suspended in ether and dilute hydrochloric acid is added. After shaking, the organic layer is washed, dried and evaporated to give d 2-(5-oxo-5H-dibenzo[a,d]cyclohepten-2-yl)propionic acid [m.p. 108°–110° C; $[\alpha]_D$+ 48.9° (chloroform)] which can be recrystallized from acetonehexane. l 2-(5-Oxo-5H-dibenzo[a,d]cyclohepten-2-yl)propionic acid can be obtained in similar manner using d-amphetamine.

EXAMPLE XIII 2.78 G. of 2-(5-oxo-5H-dibenzo[a,d]cyclohepten-2-yl)-propionic acid is stirred in a mixture of 20 ml. of benzene and 5 ml. of trifluoroacetic anhydride for 15 minutes. The mixture is evaporated to dryness and redissolved in 20 ml. of dry benzene. A mixture of 1.0 g. of pyridine and 2.44 g. (2 moles) of (+) α-phenylethanol is added. The mixture is left for 30 minutes and then water and ether is added. The organic layer is washed with dilute hydrochloric acid and water, then dried and evaporated. The residue is chromatographed on 100 g. silica gel, eluting with hexane:ether (4:1) to afford a 1:1 mixture of diastereomeric esters. Repeated crystallization of this mixture from ether-hexane yields the less soluble isomer. The purity of samples from successive recrystallizations is monitored by gas-liquid chromatography using a 1 meter × 2 mm. column packed with Chromosorb W (Regis Chemical Co., Chicago, Ill.) impregnated with 3% w/w OV101 polymeric material (Applied Sciences Laboratory, Inc., State College, Penn.) as stationary phase, and helium as the carrier gas at 220° C. The less soluble isomer is decomposed by stirring in a mixture of 5 ml. of benzene and 5 ml. of trifluoroacetic acid for 30 minutes. Water and ether are added and the ethereal layer washed with water, and then with dilute aqueous sodium carbonate. The aqueous layer is acidified with dilute hydrochloric acid and then extracted with ether. The ethereal layer is washed, dried and evaporated to give d 2-(5-oxo-5H-dibenzo[a,d]cyclohepten-2-yl)propionic acid. l 2-(5-Oxo-5H-dibenzo[a,d]cyclohepten-2-yl)propionic acid [m.p. 105°–107° C; $[\alpha]_D$ −47.4° (chloroform)] can be obtained in similar manner using (−) α-phenylethanol.

EXAMPLE XIV

This Example illustrates the use of diazoethane in the Arndt-Eistert reaction to afford 2-(5-oxo-5H-dibenzo[a,d]cyclohepten-2-yl)propionic acid without the need for α-methylation of (5-oxo-5H-dibenzo[a,d]cyclohepten-2-yl)-acetic acid as in Example II above.

2.78 G. of 2-chloroformyl-5-oxo-5H-dibenzo[a,d]cycloheptene is dissolved in 50 ml. of chloroform and added to a 3 molar excess of ethereal diazoethane at 0° C. The mixture is left for 12 hrs, then evaporated to dryness. The residue, which consists of 2-diazopropionyl-5-oxo-5H-dibenzo[a,d]cycloheptene is dissolved in 10 ml. of benzyl alcohol and 3 ml. of N,N-dimethylaniline, and heated to 170° C for 5 minutes. The mixture is cooled and evaporated to an oil which is chromatographed on 150 gm. silica gel, eluting with benzene, to afford 2-(5-oxo-5H-dibenzo[a,d]cyclohepten-2-yl)propionic acid benzyl ester. This material is refluxed for 8 hrs, in 5% aqueous potassium hydroxide, cooled and acidified to yield 2-(5-oxo-5H-dibenzo[a,d]cyclohepten-2-yl)propionic acid.

EXAMPLE XV 0.51 G. of β-N,N-dimethylaminoethyl 2-(5-oxo-5H-dibenzo[a,d]cyclohepten-2-yl)propionate is dissolved in about 25 ml. of diethyl ether and hydrochloric acid gas is passed therethrough to give a precipitate. The ether is decanted, and the precipitate washed with ether, dried under vacuum, and then recrystallized from isopropanol/ether to give β-N,N-dimethylaminoethyl 2-(5-oxo-5H-dibenzo[a,d]cyclohepten-2-yl)propionate hydrochloride (m.p. 136°–137° C).

In a similar manner using the appropriate esters prepared herein, the following compounds are prepared:

β-(morpholino)ethyl 2-(5-oxo-5H-dibenzo[a,d]cyclohepten-2-yl)propionate hydrochloride (m.p. 146°–150° C); and β-N,N-diethylaminoethyl 2-(5-oxo-5H-dibenzo[a,d]cyclohepten-2-yl)propionate hydrochloride (m.p. 117°–123° C).

EXAMPLE XVI

The procedures of Examples VIII and IX are repeated substituting d 2-(5-oxo-5H-dibenzo[a,d]cyclohepten-2-yl)-propionic acid for the 2-(5-oxo-5H-dibenzo[a,d]cyclohepten-2-yl)propionic acid to afford:

the sodium salt of d 2-(5-oxo-5H-dibenzo[a,d]cyclohepten-2-yl)propionic acid [m.p. 220°–240° C; $[\alpha]_D$ −34° (water)];

the potassium salt of d 2-(5-oxo-5H-dibenzo[a,d]cyclohepten-2-yl)propionic acid; and the calcium salt of d 2-(5-oxo-5H-dibenzo[a,d]cyclohepten-2-yl)propionic acid.

In similar manner, substituting l 2-(5-oxo-5H-dibenzo[a,d]cyclohepten-2-yl)propionic acid for the 2-(5-oxo-5H-dibenzo[a,d]cyclohepten-2-yl)propionic acid, the following compounds are prepared:

the sodium salt of l 2-(5-oxo-5H-dibenzo[a,d]cyclohepten-2-yl)propionic acid;

the potassium salt of l 2-(5-oxo-5H-dibenzo[a,d]cyclohepten-2-yl)propionic acid; and the calcium salt of l 2-(5-oxo-5H-dibenzo[a,d]cyclohepten-2-yl)propionic acid.

EXAMPLES XVII – XIX

A solution is prepared having 10 mg. of the sodium salt of d 2-(5-oxo-5H-dibenzo[a,d]cyclohepten-2-yl)propionic acid dissolved per ml. of normal saline solution.

Suspensions are prepared by substituting 20 mg. dl 2-(5-oxo-5H-dibenzo[a,d]cyclohepten-2-yl)propionic acid and 10 mg. of d 2-(5-oxo-5H-dibenzo[a,d]cyclohepten-2-yl)-propionic acid, respectively, for the sodium salt of d 2-(5-oxo-5H-dibenzo[a,d]cyclohepten-2-yl)propionic acid.

The suspensions prepared above can optionally include 0.1% Tween 80 (sorbitan monooleate polyoxyethylene; a product of Atlas Chemical Industries, Inc.).

EXAMPLE XX

| Ingredients | Quantity per tablet, mgs. |
| --- | --- |
| d 2-(5-oxo-5H-dibenzo-[a,d]cyclohepten-2-yl)propionic acid | 30 |
| cornstarch (paste) | 25 |
| magnesium stearate | 0.4 |
| lactose | to 250 |

The above ingredients are thoroughly mixed and pressed into single scored tablets.

EXAMPLE XXI

| Ingredients | Quantity per tablet, mgs. |
| --- | --- |
| d 2-(5-oxo-5H-dibenzo-[a,d]cyclohepten-2-yl)propionic acid or the sodium salt of d 2-(5-oxo-5H-dibenzo-[a,d]cyclohepten-2-yl)propionic acid | 25 |
| cornstarch | 19 |
| magnesium stearate | 0.4 |
| polyvinylpyrrolidone | 8 |
| lactose | 190 |

The above ingredients are thoroughly mixed and pressed into single scored tablets.

EXAMPLE XXII

| Ingredients | Quantity per capsule, mgs. |
| --- | --- |
| d 2-(5-oxo-5H-dibenzo-[a,d]cyclohepten-2-yl)propionic acid | 25 |
| cornstarch | 20 |
| lactose | to 200 |

The above ingredients are mixed and introduced to a hardshell gelatin capsule.

EXAMPLE XXIII

| Ingredients | Quantity per capsule, mgs. |
| --- | --- |
| The sodium salt of d-2-(5-oxo-5H-dibenzo-[a,d]cyclohepten-2-yl)propionic acid | 30 |
| lactose | 72 |
| magnesium stearate | 8 |

The above ingredients are mixed and introduced to a hard-shell gelatin capsule.

EXAMPLE XXIV

A suppository totaling 2.8 grams is prepared having the following composition:

| | |
| --- | --- |
| A suppository totaling 2.8 grams is prepared having the following composition: | |
| the sodium salt of d 2-(5-oxo-5H-dibenzo[a,d]cyclohepten-2-yl)propionic acid | 10–50 mg. |
| Witepsol H-15 (triglycerides of saturated vegetable fatty acids; a product of Riches-Nelson, Inc. New York, N.Y.) | balance |

EXAMPLE XXV

The anti-inflammatory activity of the following compounds embraced within this invention was compared with the activity of phenylbutazone by means of the carrageenin-induced rat paw inflammation test described below.

TEST FOR ANTI-INFLAMMATORY ACTIVITY UTILIZING CARRAGEENIN INDUCED PAW INFLAMMATION IN THE RAT

MATERIALS AND METHODS

Female rats weighing 80–90 grams are used. The test materials are given at hour 0 orally by gavage in 1 ml. aqueous vehicle. At hour 1, 0.05 ml. of a 1% solution (in 0.9% NaCl) of carrageenin is injected into the right hind paw. This injection causes an inflammation of the paw. The rats are sacrificed at hour 4, at which time both hind paws are removed and weighed separately.

End point: % increase in paw size calculated as follows:

$$\frac{\text{Wt. of Right Paw} - \text{Wt. of Left Paw}}{\text{Wt. of Left Paw}} \times 100$$

The results of these tests are summarized in the following table:

| Compound | Oral Anti-Inflammatory Activity (Phenylbutazone = 1) |
|---|---|
| 2-(5-oxo-5H-dibenzo[a,d]cyclohepten-2-yl)-propionic acid | 49 |
| d 2-(5-oxo-5H-dibenzo[a,d]cyclohepten-2-yl)-propionic acid | 71 |
| sodium 2-(5-oxo-5H-dibenzo[a,d]cyclohepten-2-yl)-propionate | 50 |
| isopropylammonium 2-(5-oxo-5H-dibenzo[a,d]cyclohepten-2-yl)propionate | 40 |
| methyl 2-(5-oxo-5H-dibenzo[a,d]cyclohepten-2-yl)-propionate | 10 |
| $\beta$-N,N-diethylaminoethyl 2-(5-oxo-5H-dibenzo[a,d]-cyclohepten-2-yl)propionate | 14 |
| $\beta$-(morpholino)ethyl 2-(5-oxo-5H-dibenzo[a,d]cyclo-hepten-2-yl)propionate | 6 |
| 2-(5-oxo-5H-dibenzo[a,d]-cyclohepten-2-yl)butyric acid | 7 |

Certain of the above compounds were also tested for analgesic activity in the mouse analgesic (anti-writhing) assay and were found to have substantial analgesic activity relative to aspirin.

EXAMPLE XXVI

In similar manner to the procedure of Example V, substituting tridecanol, hexadecanol and eicosanol for the isopentyl alcohol, there is prepared:

tridecyl 2-(5-oxo-5H-dibenzo[a,d]cyclohepten-2-yl)-propionate,
hexadecyl 2-(5-oxo-5H-dibenzo[a,d]cyclohepten-2-yl)-propionate, and
eicosyl 2-(5-oxo-5H-dibenzo[a,d]cyclohepten-2-yl)-propionate (m.p. 63°–64° C).

While the present invention has been described with reference to specific embodiments thereof, it should be understood by those skilled in this art that various changes may be made and equivalents may be substituted without departing from the true spirit and scope of the invention. In addition, many modifications can be made to adapt a particular situation, material or composition of matter, process, process step or steps, or then-present objective to the spirit of this invention without departing from its essential teachings.

What is claimed is:

1. A compound selected from the group of compounds represented by the formula:

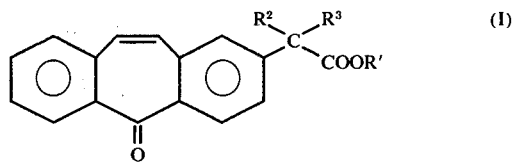

where R' is hydrogen, alkyl having 1 to 12 carbon atoms, or

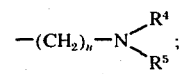

n is an integer from 2 through 4, inclusive; $R^4$ and $R^5$ are independently lower alkyl having 1 to 6 carbon atoms; one of $R^2$ and $R^3$ is hydrogen and the other is hydrogen, methyl, or ethyl, or together $R^2$ and $R^3$ are methylene; and the pharmaceutically acceptable salts thereof.

2. The compound of claim 1 where R' is hydrogen.
3. The compound of claim 1 where R' is alkyl having 1 to 12 carbon atoms.
4. The compound of claim 1 where R' is

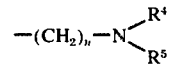

and $R^4$ and $R^5$ are independently lower alkyl.

5. The compound of claim 1 where both $R^2$ and $R^3$ are hydrogen.
6. The compound of claim 1 where said compound of Formula I is (5-oxo-5H-dibenzo[a,d]cyclohepten-2-yl)acetic acid.
7. The compound of claim 1 wherein said compound is the sodium, potassium or calcium salt of 2-(5-oxo-5H-dibenzo[a,d]cyclohepten-2-yl)acetic acid.
8. The compound of claim 1 where said compound of Formula I is 2-(5-oxo-5H-dibenzo[a,d]cyclohepten-2-yl)butyric acid.
9. The compound of claim 1 where said compound of Formula I is 2-(5-oxo-5H-dibenzo[a,d]cyclohepten-2-yl)acrylic acid.
10. A compound selected from the group of compounds represented by the formula:

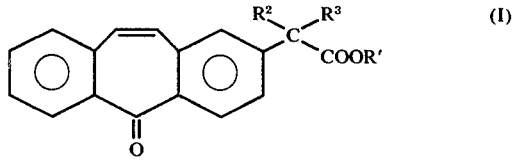

where R' is hydrogen, alkyl having 1 to 12 carbon atoms, or

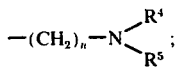

$n$ is an integer from 2 through 4, inclusive; $R^4$ and $R^5$ are independently lower alkyl having 1 to 6 carbon atoms; one of $R^2$ and $R^3$ is hydrogen and the other is methyl; and the pharmaceutically acceptable salts thereof.

11. The compound of claim 10 wherein R' is alkyl having 1 to 12 carbon atoms.

12. The compound of claim 10 wherein R' is

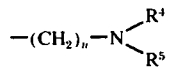

where $R^4$ and $R^5$ are independently lower alkyl.

13. 2-(5-oxo-5H-dibenzo[a,d]cyclohepten-2-yl)propionic acid.

14. The compound of claim 10 wherein said compound is the sodium, potassium, or calcium salt of 2-(5-oxo-5H-dibenzo[a,d]cyclohepten-2-yl)propionic acid.

15. The compound of claim 10 wherein said compound is the sodium salt of 2-(5-oxo-5H-dibenzo[a,d]cyclohepten-2-yl)propionic acid.

16. The compound of claim 10 wherein said compound is isopentyl 2-(5-oxo-5H-dibenzo[a,d]cyclohepten-2-yl)propionate.

17. The compound of claim 10 wherein said compound is dodecyl 2-(5-oxo-5H-dibenzo[a,d]cyclohepten-2-yl)propionate.

18. The compound of claim 10 wherein said compound is β-N,N-dimethylaminoethyl 2-(5-oxo-5H-dibenzo[a,d]cyclohepten-2-yl)propionate.

19. The compound of claim 10 wherein said compound is β-N,N-diethylaminoethyl 2-(5-oxo-5H-dibenzo[a,d]cyclohepten-2-yl)propionate.

20. The compound of claim 10 wherein said compound is β-N,N-methylethylaminoethyl 2-(5-oxo-5H-dibenzo[a,d]cyclohepten-2-yl)propionate.

21. d 2-(5-oxo-5H-dibenzo[a,d]cyclohepten-2-yl)propionic acid.

22. The compound of claim 10 wherein said compound is the sodium, potassium or calcium salt of d 2-(5-oxo-5H-dibenzo[a,d]cyclohepten-2-yl)propionic acid.

23. The compound of claim 10 wherein said compound is the sodium salt of d 2-(5-oxo-5H-dibenzo[a,d]cyclohepten-2-yl)propionic acid.

24. The compound of claim 10 wherein said compound of Formula I is 1 2-(5-oxo-5H-dibenzo[a,d]cyclohepten-1-yl)propionic acid.

25. The compound of claim 10 wherein said compound is the sodium salt of 1 2-(5-oxo-5H-dibenzo[a,d]cyclohepten-2-yl)propionic acid.

26. A compound selected from the group consisting of 2'-carboxyphenyl 2-(5-oxo-5H-dibenzo[a,d]cyclohepten-2-yl)propionate, 2'-carbomethoxyphenyl 2-(5-oxo-5H-dibenzo[a,d]cyclohepten-2-yl)propionate, and phenyl 2-(5-oxo-5H-dibenzo[a,d]cyclohepten-2-yl)propionate.

* * * * *